United States Patent [19]
Keogh et al.

[11] Patent Number: 5,669,892
[45] Date of Patent: Sep. 23, 1997

[54] OVERFILL PROTECTION FOR SUCTION DRAINAGE SYSTEM

[75] Inventors: Alan P. Keogh, Donegal Town; John J. Ferris; Pascal J. Maher, both of Donegal, all of Ireland

[73] Assignee: Abbott Laboratories, Abbott Park, Ill.

[21] Appl. No.: 526,656

[22] Filed: Sep. 11, 1995

Related U.S. Application Data

[63] Continuation of Ser. No. 173,537, Dec. 27, 1993, abandoned.

[51] Int. Cl.$^6$ ............................................. A61M 1/00
[52] U.S. Cl. ............................................. 604/320
[58] Field of Search ............................. 604/317–323

[56] References Cited

U.S. PATENT DOCUMENTS

| | | | |
|---|---|---|---|
| 3,938,540 | 2/1976 | Holbrook et al. | 604/320 |
| 4,256,109 | 3/1981 | Nichols | 128/276 |
| 4,379,455 | 4/1983 | Deaton | 604/320 |
| 4,465,485 | 8/1984 | Kashmer et al. | 604/320 |
| 4,487,606 | 12/1984 | Leviton et al. | |
| 4,507,120 | 3/1985 | Paradis | 604/320 |
| 4,764,167 | 8/1988 | Tu | |
| 5,158,007 | 2/1993 | Middaugh et al. | 604/320 |
| 5,185,007 | 2/1993 | Middaugh et al. | 604/320 |

FOREIGN PATENT DOCUMENTS

| | | |
|---|---|---|
| 0358302 | 3/1990 | United Kingdom . |
| WO8700439 | 1/1987 | WIPO . |
| WO9325248 | 12/1993 | WIPO . |

*Primary Examiner*—Mark Bockelman
*Assistant Examiner*—Ellen Tao
*Attorney, Agent, or Firm*—David C. Hannum

[57] ABSTRACT

The present invention is directed to a shut-off valve for a suction drainage system wherein flow of waste to a disposable container is stopped at a pre-determined volume which is less than the maximum capacity. A tubular sleeve is coaxially located around the shut-off valve. The shut-off below the maximum volume allows a safety margin for the waste container to be capped off without spilling or geysering.

1 Claim, 2 Drawing Sheets

5,669,892

OVERFILL PROTECTION FOR SUCTION DRAINAGE SYSTEM

This application is a continuation of application Ser. No. 08/173,537, filed Dec. 27, 1993 now abandoned.

FIELD OF THE INVENTION

This invention relates to a suction drainage system used in hospitals to collect waste fluids during surgical or other patient procedures. More specifically, the present invention relates to an overfill protection apparatus associated with the shutoff valve for a suction drainage system that prevents the overfilling of the waste fluid container or provides extra clearance in a waste fluid container so that a waste treating material can be added.

BACKGROUND OF THE INVENTION

For many years, hospitals have been using suction draining systems to collect waste fluids from surgery and other procedures. The waste fluid is collected into a sealed collection container, preferably a disposable container such as flexible bag or liner. The suction draining system has a fluid flow connection from the disposable container to the body of a patient and an air flow connection from the disposable container to a suction source. The waste fluids being collected are often highly infectious and therefore extreme care must be used during collection and disposal. Precautions must be taken to minimize the exposure of healthcare providers, workers, and other patients to the collected waste due to spills or other failures of the system.

Suction draining systems in use today usually include a shut-off valve, typically associated with the air flow suction line so as to shut-off the suction source when the waste fluid in the disposable container reaches a predetermined volume. The shut-off valve prevents infectious waste from entering and contaminating the hospital suction system. Without a shut-off valve, the suction source may accidentally pull waste fluid from an over-filled collection chamber into the hospital suction (vacuum) system.

Most shutoff valves are activated by the level or volume of the collected waste fluid in the collection container. As the volume of waste fluid approaches the capacity of the container, the fluid activates the shut-off valve to end the further flow of waste fluids into the container. The disposable liner can then be safely disconnected from the suction system, sealed, and disposed of in a safe and proper manner.

In certain procedures it is desirable to have the flexibility to shut-off the flow of waste fluid into a flexible collection container when a predetermined fluid volume is reached before the maximum fill capacity volume is reached. For example, shutting-off the fluid flow before the maximum fill capacity volume is reached allows the disposable collection container to be capped (sealed) and removed from the rigid container with less risk of spilling or geysering.

For other suction drainage procedures, it is desirable to add a waste-treating material such as a germicide and/or a gelling agent to the aspirated waste fluid in the disposable collection container. The waste treating material neutralizes the waste fluid and minimizes risk of exposure due to accidental spill or failure of the system after the fluid has been collected. Thus, it is desirable to automatically provide for an extra clearance volume needed to accommodate the added waste-treating material, when the waste-treating material is specified.

Accordingly, it is an object of the present invention to provide protection against overfilling for a suction drainage system.

It is another object of the present invention to provide flexibility in filling the collection container to a volume less than capacity that allows a germicide or an absorbent to be safely introduced into the predetermined volume reserved in the disposable collection container.

SUMMARY OF THE INVENTION

The present invention is directed to a fill or overfill control for a suction drainage system.

More particularly, the present invention is directed to overfill protection that is associated with the shut-off valve for a suction drainage system so that flow of waste fluid to the disposable waste collection container is stopped at a predetermined volume which is less than the container maximum capacity.

Alternatively, the present invention is directed to overfill protection that activates the suction drainage shut-off valve at a volume of the disposable container that is a sufficient volume less than the maximum capacity to allow a waste treating material such as a germicide and/or an absorbent to be added to the collected waste.

Other advantages and features of the present invention will become apparent from the following detailed description, the accompanying drawings, and the appended claims.

DETAILED DESCRIPTION OF THE PREFERRED EMBODIMENTS

Figures 1, 2:
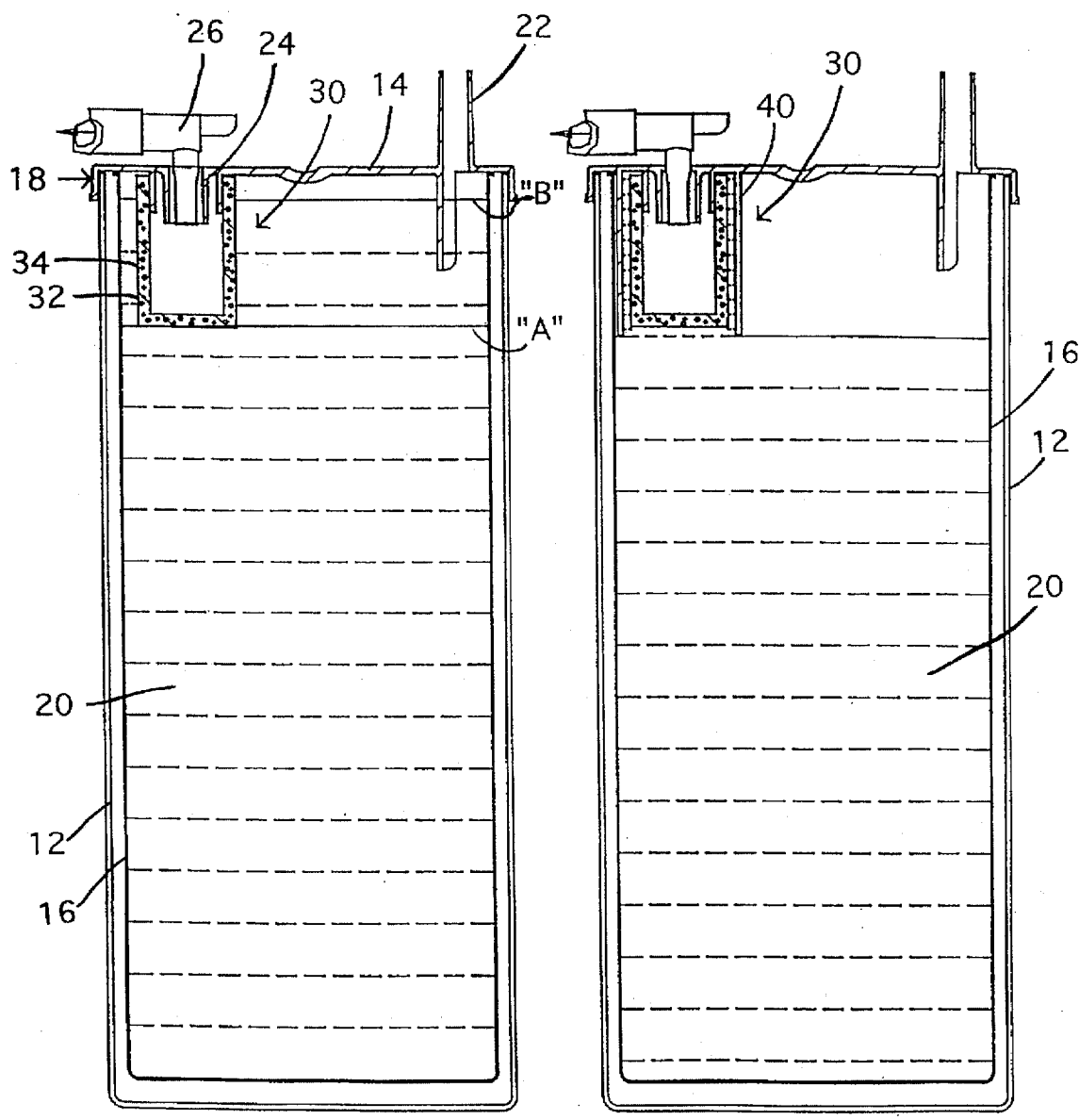
FIG. 1 is a schematic sectional view of a waste container having a disposable flexible liner and a non-mechanical shut-off valve.
FIG. 2 is a schematic sectional view of a waste container having a disposable flexible liner and a non-mechanical shut-off valve with overfill protection according to the present invention.

The present invention is capable of embodiments in various forms. There is shown in the drawings and there will hereinafter be described several presently preferred embodiments, with the understanding that the present disclosure is to be considered as an example of the invention, and is not intended to limit the invention to the specific embodiments illustrated.

Referring to the drawings, FIG. 1 is a schematic section of a suction drainage system. The system includes a rigid re-usable container 12, a rigid lid 14 and preferably a disposable flexible liner 16. Alternatively, the rigid container may be used once without a flexible liner and then disposed.

The container 12 is preferably made of a rigid plastic material and is open at the top and closed at the bottom. In a preferred form, the container 12 is transparent to allow visual monitoring of the system. Also preferably the container 12 is cylindrical for manufacturing purpose although the specific shape is not important.

The lid 14 is also made from a rigid plastic material and preferably has an axial depending skirt 18 for fluid tight engagement with the open end of the container 12. Preferably the disposable flexible bag or liner 16 is fixed to the underside of the lid 14 in a fluid tight manner. The lid 14 and the liner 16 define a sealed collection chamber 20 in which waste fluid is collected and later disposed.

The flexible liner 16 is suspended from the underside of the lid 14. The upper end of the liner 16 is fused or sealed onto the underside of the lid 14 in a completely fluid tight manner. Preferably flexible liner 16 is made of substantially transparent rubber-like flexible material or thermoplastic material. The liner 16 may be blow molded from a plastic such as polyvinyl chloride (PVC), so as to eliminate weak areas such as seams.

In the suction drainage embodiment illustrated in FIG. 1, for example, rigid container 12 surrounds the flexible liner 16 in a protective manner. The skirt portion 18 provided on the lid 14 fits over the open end of the container 12 in fluid tight engagement. Preferably, container 12 does not come in contact with the waste material, so it may be repeatedly used without sterilization. Alternatively, as previously discussed, a disposable rigid container (not shown) similar to container 12 may be used without a flexible liner. Such a container may be filled once and is then disposed with the collected waste fluid in the proper manner.

Lid 14 includes an inlet port 22 and an outlet port 24, both of which open into the sealed collection chamber 20 defined by lid 14 and flexible liner 16 (or alternatively by a lid and rigid disposable container). The inlet port 22 directs incoming waste to the bottom of the collection chamber 20.

An inlet tubing line (not shown) connects the source of the fluid to be drained, such as a patient surgical site, to the inlet port 22.

Outlet port 24 projects upward from and is sealed to the lid 14. The outlet fitting 26 extends from the outlet port 24 and is connected to a negative pressure or vacuum source for facilitating operation of the suction drainage system.

As discussed earlier, a shut-off valve is preferably included in the suction drainage system to prevent the aspirated waste from directly contacting and contaminating the hospital vacuum system. The shut-off valve 30 is mounted in association with the suction line at the outlet port 24.

In a preferred embodiment of the suction drainage system shown in FIG. 1, the shut-off valve 30A is a non-mechanical valve. The valve includes a housing 32 that contains a polyethylene foam 34. The foam contains air flow passages and swellable moisture sensitive particles made of polymers or other suitable materials. A suitable non-mechanical shut-off valve is disclosed in published PCT application No. WO 87/00439.

The above described shut-off valve and others like it permits normal airflow through the air flow passages in any unwet part of the shut-off valve. However as the valve becomes wet, the polymer particles swell to block the air flow passages.

With reference to FIG. 1, during the suction drainage procedure, the level of the waste fluid received into the chamber 20 increases to the level marked "A" and continues to increase to the level marked "B". At level "B" the waste fluid flow into the collection chamber 20 is completely shut off because all the flow passages through the foam 34 are blocked. Also, there is very little empty volume above the collected fluid level in the chamber 20 to accommodate handling of the flexible chamber as it is capped and/or removed. Also there may not be sufficient remaining volume in chamber 20 for the addition of a neutralizing agent such as a germicide or a gelling agent.

FIG. 2 shows a preferred embodiment of a shut-off valve with an overfill protection sleeve 40 according to the present invention. The non-mechanical shut-off valve 30 is a hollow cylinder having an open end attached to the lid 14 and a closed end extending into the sealed collection chamber 20. The overfill protection sleeve 40 is a rigid tubular sleeve axially extending downward from the lid 14. The sleeve 40 can be integrally molded or otherwise fabricated with the lid 14 or can be attached to the lid by any suitable attaching technique. The sleeve 40 has an interior surface coaxially extending with and closely surrounding the exterior surface of the shut-off valve 30. The length of the sleeve 40 relative to the length of the shut-off valve 30 is predetermined so as to cause the waste fluid received in the collection chamber to activate the shut-off valve 30 when the received waste fluid reaches the level of the sleeve 40 in the collection chamber 20. When the fluid level reaches the sleeve level, vacuum from the suction source causes the fluid to climb up the small volume between the sleeve and the valve. As the fluid collected wets the valve 30, the fluid activates the valve so as to shut off the suction line from the suction source and prevent additional waste fluid from being sucked into the sealed chamber 20.

The additional clearance volume allowed by the length of the sleeve provides some "give" in the filled flexible liner during capping and removal that may prevent leakage, spilling or worse. The length of the sleeve 40 can be varied so as to determine the volume to be left unfilled with out need for changing the shut-off valve configuration. Thus suction liners currently being manufactured can have a predetermined length of sleeve added as described with respect to this presently disclosed invention to result in a predetermined fluid volume in the collection container without changing the configuration of the shut-off valve.

Figure 1A:
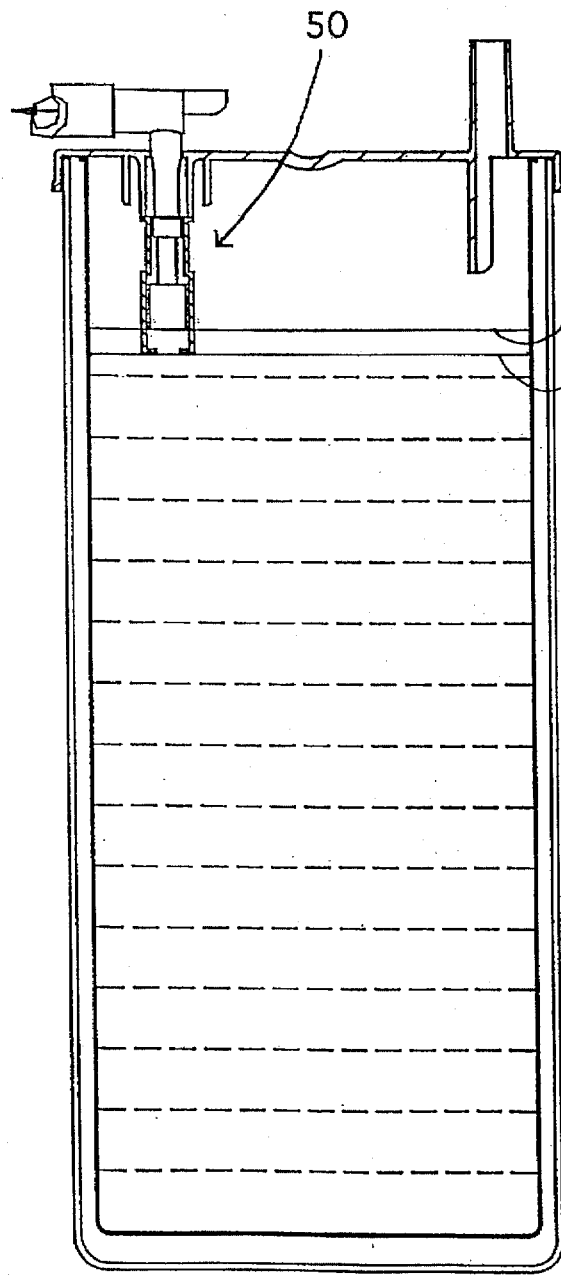
FIG. 1A is a schematic sectional view of a waste container having a disposable flexible liner and a mechanical float shut-off valve.
Figure 2A:
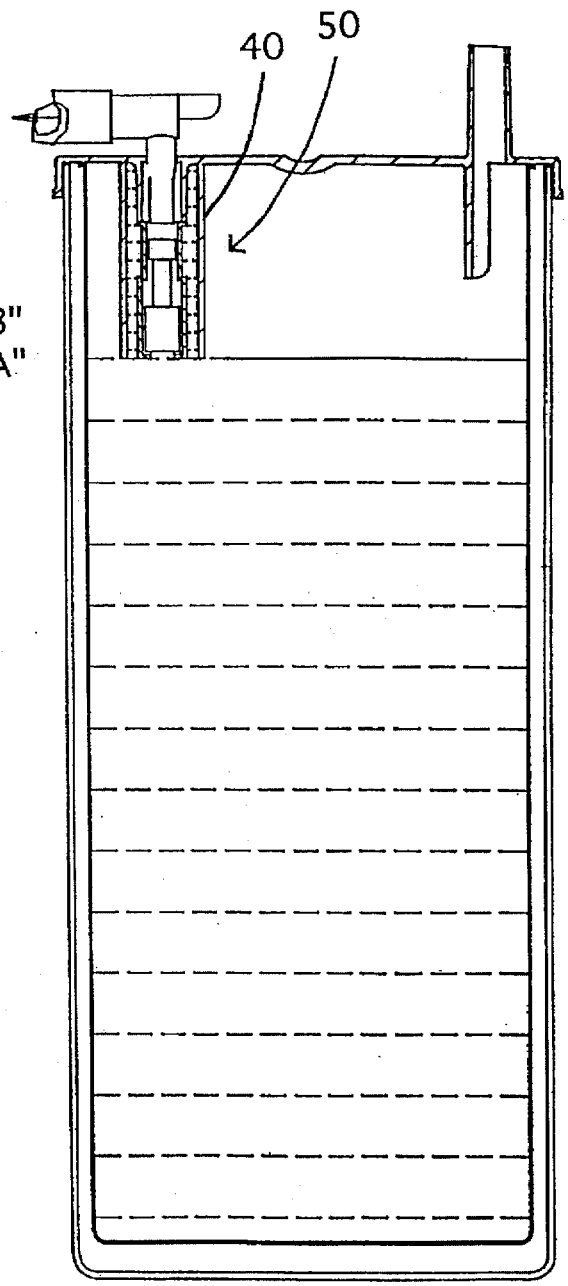
FIG. 2A is a schematic sectional view of a waste container having a disposable flexible liner and a mechanical float shut-off valve with overfill protection according to the present invention.

An alternative embodiment having a mechanical float type valve is shown in FIGS. 1A and 2A. The tubular sleeve positioned around the mechanical float valve 50 raises the liquid height around any standard float valve to a level above the level in the container chamber 20 and allows the float shut-off valve to be activated at a predetermined volume which is less than the actual container capacity volume for the height of the valve in the container.

The foregoing invention can now be practiced by those skilled in the art. Such skilled persons will appreciate that the overfill protection of the present invention is not necessarily restricted to the particular embodiments presented herein. The scope of the present invention is to be defined by the terms of the following claims in the spirit and meaning of the preceding description.

We claim:

1. A system for collecting fluid from a fluid source, the system comprising:

a container having a lid defining a chamber for receiving fluid;

a fluid inlet port formed in said container, said inlet port in fluid communication with an upper portion of the chamber;

an outlet port formed in the lid of in said container, said outlet port in fluid communication with an upper portion of the chamber, said outlet port constructed for connecting the chamber to a suction source;

a fluid-activated shut-off valve associated with said outlet port, said shut-off valve extending into the chamber; and a sleeve, said sleeve extending from said lid of said container, and surrounding said shut-off valve, and extending further into the chamber than said shut-off valve, said sleeve having a distal portion located within the chamber and beyond the shut-off valve, said distal portion having an open end, said chamber in fluid communication with said outlet port via only said distal portion of said sleeve, whereby received fluid reaching the level defined by said open end of said sleeve is drawn by suction into the sleeve to cause said fluid-activated valve to close the outlet port while the level of fluid in the chamber remains at the level defined by said open end of said sleeve.

* * * * *